United States Patent [19]

Bergman et al.

[11] Patent Number: 4,804,537

[45] Date of Patent: Feb. 14, 1989

[54] SPERM SELECTION PROCESS USING A SALT OF HYALURONIC ACID

[75] Inventors: Per O. Bergman, Göteborg; Yvonne M. Steen, Västra Frölunda; Björn G. Ingelman, Uppsala, all of Sweden

[73] Assignee: Pharmacia AB, Uppsala, Sweden

[21] Appl. No.: 60,360

[22] PCT Filed: Oct. 17, 1986

[86] PCT No.: PCT/SE86/00484

§ 371 Date: May 22, 1987

§ 102(e) Date: May 22, 1987

[87] PCT Pub. No.: WO87/02382

PCT Pub. Date: Apr. 23, 1987

[30] Foreign Application Priority Data

Oct. 18, 1985 [SE] Sweden .............................. 8504872-6

[51] Int. Cl.[4] ........................................... A61K 35/48
[52] U.S. Cl. ......................................... 424/105; 435/2
[58] Field of Search ............................. 424/105; 435/2

[56] References Cited

U.S. PATENT DOCUMENTS 4,007,087  2/1977  Ericsson .................................. 435/2
4,327,177  4/1982  Shrimpton .............................. 435/2

OTHER PUBLICATIONS

Pola Chemical–Chem. Abst. vol. 94 (1981), p. 109,088b.
Kurbatov–Chem. Abst., vol. 87 (1977) p. 2774a
Pola Chemical–Chem. Abst. vol. 94, (1981), p. 109,091x.

*Primary Examiner*—Sam Rosen
*Attorney, Agent, or Firm*—Fred Philpitt

[57] ABSTRACT

The present invention relates to a process and means for separating motile sperm cells in vitro from an aqueous sperm-containing sample by means of contacting said sample with a layer of an aqueous artificial penetration medium for sperm cells, said medium having incorporated therein a water-soluble physiologically acceptable salt of hyaluronic acid, whereby motile sperm cells are caused to migrate into said layer from said sperm-containing sample. The invention also comprises fertilization with sperm cells separated in this manner.

3 Claims, No Drawings

SPERM SELECTION PROCESS USING A SALT OF HYALURONIC ACID

The present invention relates to an improved in vitro process for the selection of motile sperm from a fluid sample, for instance an ejaculate. The invention comprises also an improved means for said selection process.

Involuntary childlessness is a great problem for those concerned; much work is therefore dedicated to exploring the causes of that condition. As far as the male partner is concerned, attention is chiefly directed to the quality of the sperm sample in respect of sperm concentration in the ejaculate, and to sperm cell morphology and motility. It appears that among these criteria sperm concentration is the one that has been relied on more than the others in the common routines for fertility status assessments. A fresh ejaculate will normally exhibit a broad spectrum of motilities of different sperm cells, comprising the entire range from cells having excellent motility properties and moving fast in a forward direction, down to sperm cells characterized by erratic movements or total immobility. Therefore, fertility assessments based only on the number of sperm cells present in a given volume of fluid will not be reliable; a qualitative analysis of sperm motility provides a far better basis for male fertility evaluation. Sperm movement velocities and relative proportions of motile sperm in a sperm sample have been studied by means of numerous methods, e.g. Kremer's (Int. J. Fertil. 10/1965/, p. 209–215), see also for example L. Blasco in Fertility and Sterility 41(1984) p. 177–192. These and other articles describe attempts made to investigate the ability of sperm to penetrate cervical mucus. In these experiments cervical mucus is aspirated into a capillary tube sealed at one end, whereupon the other end is contacted with seminal fluid (optionally diluted) or with a suspension of sperm cells isolated from seminal fluid. After a suitable period of time the tubes are studied in a microscope, and the number of sperm that have penetrated the mucus medium is evaluated. It is difficult however to standardize a test of this type because the quality of the cervical mucus will vary from female to female and even in the same female during various periods of the menstrual cycle. Moreover cervical mucus samples are hard to come by and contain components which make them unsuitable for in vitro methods. Cervical mucus samples have poor storage properties, are difficult to sterilize and involve a hazard in respect of transmission of contagious agents.

To avoid the drawbacks of the natural penetration medium for sperm (i.e. the cervical mucus), substitutes therefore have come into use which consist of solutions of various substances in water. In the following description and in the claims such a substitute will be referred to as "aqueous artificial penetration medium for sperm" (or simply "penetration medium" or "medium") as in contrast to the aforesaid natural penetration medium for sperm. Various types of such artificial media have been described heretofore. Physiological salt solutions employed for this purpose have contained low molecular substances and sometimes also macromolecular substances like for instance albumin. Such solutions are given pH values within a range suitable for and physiologically acceptable to sperm (e.g. by means of adding a physiologically acceptable buffer), and they may contain substances physiologically acceptable to sperm such as e.g. salts, nutrients, activating substances, substances exerting an influence on capacitation, trace elements etc. Examples of these are substances occurring in blood plasma och blood serum (serum being a suitable additive to such media). It is also possible by means of additives to control the osmotic pressure of the solutions so as to obtain values suitable for sperm. The solutions may also contain additives preventing microorganism growth in the medium, such as e.g. antibiotics. There is a comprehensive literature describing suitable solutions in which sperm are able to survive and to retain their motility and fertilizing capacity, these solutions being useful as penetration media.

They consist of for instance well-known physiological media the names of which, too, are well-known to the skilled artisan: e.g. Ringer, Krebs-Ringer, Thyrode, BWW, Ham, HAT, Baker, Eagle, Earl etc., optionally modified by means of e.g. further additives like for example buffer substances, albumin or serum. (Some examples are given in the following reference publications: Ericsson et al. Nature 246(1973) p. 421–424, Lopata et al., Fertility and Sterility 27(1976) p. 677–684, Koper et al., Br. J. Urology 51(1979) p. 587–590, Wolf et al., J. Andrology 3(1982) p. 445–451, Beernik et al., Fertility and Sterility 38(1982) p. 493–495, and Prasad Int J. Andrology 7(1984) p. 5–22).

When the selected sperm are to be employed for fertilization it is imperative that they be free from defects. They have to be capable of fertilization, possess good motility and exhibit an intact enzyme production e.g. of hyaluronidase, and the medium in which such sperm are present should be of a type that is favourable to the egg.

There are various ways of accomplishing the selection of sperm having satisfactory motility by means of a layer of penetration medium into which the sperm cells are allowed to migrate. The commonest way of proceeding involves superposing a layer of penetration medium upon the fluid sample containing the sperm, and then allowing motile sperm to swim upwardly into the superimposed layer. Another way of proceeding comprises for example an arrangement where a layer of the penetration medium is placed below the sperm-containing fluid sample, the sperm cells then having to swim downward into the subjacent layer. The density of the medium and the density of the fluid sample are chosen so as to properly suit the procedure. As a rule the layer of penetration medium is an entirely homogeneous phase; but feasible alternative procedures involve making arrangements for sperm migration through a plurality of layers of slightly differing compositions, or the sperm may be made to pass through a layer that has a concentration gradient in respect of one or more substances present in the medium.

The procedure for selecting the sperm by way of their migrating into the artificial penetration medium may be utilized diagnostically. One may study, for instance, the number of sperm migrating into the layer and the rate at which they are moving. The procedure furthermore may be utilized for the selection of sperm possessing good motility, to be employed for fertilization. In this case sperm cells that have migrated into the layer of penetration medium are separated, and if required the sperm suspension thus withdrawn is concentrated by means of e.g. centrifugation, with subsequent resuspension in a smaller volume of the same medium or of another medium.

For example, Wolf and Sokoloski (Journal of Andrology 3(1982) p. 445–451) and Prasad (Journal of Andrology 7(1984) p. 5–22) describe a process in which a specified amount of seminal fluid on the bottom of a test tube is contacted with an albumin-containing medium that has been carefully layered onto the medium underneath. The tube is then tilted slightly into an oblique position so as to increase the contact surface between the media, whereupon penetration is permitted to proceed for about 1 hr at 37° C. The supernatant is removed, the sperm therein being concentrated by centrifugation which is then followed by washing by means of a repeated resuspension-centrifugation procedure. The final sperm pellet is resuspended in a suitable medium and the amount of sperm is determined.

However the procedure most commonly employed for in vitro fertilization is still the following: Seminal fluid diluted with an albumin-containing medium is centrifuged down into a test tube, the supernatant is removed, and the pellet of solid material at the bottom of the tube is resuspended. This process is optionally repeated several times in order to achieve efficient washing. It should be noted that this mehod does not separate viable motile sperm from defective non-motile sperm and other insoluble components of the original sample.

In view of the fact that prior art technique is not entirely satisfactory there is a major demand for an improved, simple, reproducible and mild process for the selection of motile sperm from among defective sperm and other components with the aid of a penetration medium for sperm. An improved process is desirable both for quantitative and for qualitative analyses of sperm motility as well as for other purposes like for instance preparing sperm material for in vitro and in vivo fertilizations.

We have now found that the process of selecting motile sperm cells with the aid of a penetration medium as set forth above may be improved considerably if the penetration medium is made to contain an addition of a hyaluronic acid salt which is physiologically acceptable to sperm cells, is soluble in water, and thus is present in a dissolved state in the medium. Supplementing the aqueous artificial penetration medium for sperm cells so as to make it contain additionally a water-soluble, physiologically acceptable salt of hyaluronic acid has surprisingly been found to be a very favourable expedient. The improved penetration medium is intended in the first place for human sperm selection screening but may be employed also for selection operations with other types of sperm, preferably sperm from mammals as e.g. sperm of domestic animals.

The present invention thus relates to: A process for separating motile sperm cells in vitro from an aqueous sperm-containing sample by means of contacting the sample with a layer of an aqueous artificial penetration medium for sperm cells, whereby motile sperm cells are caused to migrate from said sperm-containing sample into said layer, characterized in that a water-soluble physiologically acceptable salt of hyaluronic acid has been incorporated in said penetration medium.

The invention also comprises a process as aforesaid characterized in that sperm cells which have migrated into the layer of penetration medium are recovered, e.g. for fertilization as for instance in vitro fertilization.

The invention comprises also fertilization, for instance in vitro fertilization, characterized by employing sperm cells obtained as asforesaid.

Moreover the present invention also comprises the means for carrying out the said process, that is: an aqueous artificial penetration medium for sperm cells, characterized by having incorporated therein a water-soluble physiologically acceptable salt of hyaluronic acid.

The invention also comprises the use of a water-soluble physiologically acceptable salt of hyaluronic acid as a component in an aqueous artificial penetration medium for sperm cells.

Also, by means of the process of this invention sperm cells moving at different rates can be separated from one another, due to the fact that within a given time these different sperm cells will have covered different distances within the layer of penetration medium. When desired, sperm samples may be taken from different levels of said layer, or the sperm cells may be allowed to migrate into still another liquid layer where they are then recovered. The invention of course comprises this embodiment also.

Hyaluronic acid including also its salts (hyaluronates) is a polysaccharide having very special properties and obtainable from e.g. cockscombs or by means of culturing certain types of microorganisms. Due to the biological, chemical and physico-chemical properties of this polysaccharide the incorporation of a water-soluble physiologically acceptable salt of the polyacid hyaluronic acid (i.e. a water-soluble physiologically acceptable hyaluronate) into the penetration medium for sperm will make said medium eminently useful for the purpose contemplated. As regards the choice of a particular water-soluble physiologically acceptable salt of hyaluronic acid, this will be in the first place the sodium salt (sodium hyaluronate) although other water-soluble physiologically acceptable salts may be used. Furthermore also, the salt may be a mixed salt, with two or more positive ions present as counter-ions to the hyaluronic acid carboxyls. Such positive ions may be for example two or more of the positive ions occurring in blood plasma and in crystalloid substitute solutions for blood plasma and which are commonly employed in penetration media for sperm. These ions may be chosen to be present in e.g. such proportions inter se as to be of substantially the same order of magnitude as the physiological proportions of these ions in body fluids as e.g. in blood plasma, uterine fluid and semen; this means, thus, that there will be more sodium ions than potassium ions etc. Conceivably also physiologically acceptable organic amines may be utilized as the salt formers; but it is preferred that the hyaluronic acid is present in the medium as its sodium salt or substantially as its sodium salt and in equilibrium with the ions of the penetration medium itself. It is suitable for the medium to contain physiological concentrations of sodium and potassium ions.

Water-soluble physiologically acceptable salts of hyaluronic acid can be obtained with average molecular weights ($\overline{M}_w$) within a very wide range depending on origin, manner of preparation and, where applicable, fractionation. The average molecular weight ($\overline{M}_w$) may be for example higher than 10,000, e.g. higher than 50,000 as for instance higher than 100,000 while being for example lower than 20,000,000, e.g. lower than 10,000,000 as for instance lower than 5,000,000. In certain circumstances a high molecular product is chosen having an average molecular weight ($\overline{M}_w$) exceeding 50,000, e.g. exceeding 100,000, the $\overline{M}_w$ being lower than for instance 10,000,000 or 5,000,000. Hyaluronates with a molecular weight of up to about 4,000,000 are commercially available as well as depolymerized hyaluronates with a molecular weight of e.g. a few hundred thousand or even lower.

By means of the hyaluronate addition it is also possible to give the penetration medium a viscosity which is suitable for the medium and variable in a desired manner, depending on the experimental conditions and on the object to be achieved with the sperm penetration procedure. A too high viscosity of the medium ought to be avoided as this will slow down the speed too much with which the sperm cells are moving. Therefore, the penetration medium is preferably given a viscosity lower than 300 cP (centipoises, zero shear viscosity, at 37° C.). In many cases it is preferred that the viscosity is lower than 100 cP, as for instance lower than 50 cP or even lower than e.g. 30 cP. The viscosity of the medium is higher than 1 cP, for example in most cases higher than 2 cP, for instance higher than 5 cP, e.g. higher than 10 cP. It will of course be appreciated that the higher the average molecular weight chosen for the product the lower the amount of additive will be required for obtaining a desired viscosity.

Variably depending on the experimental conditions and on the object to be achieved by means of the sperm penetration procedure, the average molecular weight and concentration of hyaluronate may be chosen such as to represent an optimum in each individual case. The hyaluronate concentration in the penetration medium is preferably chosen higher than 0.05 mg per ml. In many cases it is preferred that the concentration is higher than 0.1 mg, e.g. higher than 0.2 mg per ml. The concentration is preferably lower than 10 mg per ml. In many cases it is preferred that the concentration is lower than 5 mg, e.g. lower than 2 mg per ml. In most cases the concentration is preferably chosen not higher than that the viscosity is lower than 300 cP, e.g. lower than 100 cP as mentioned above. If the object to be achieved e.g. is a diagnostic procedure, it has been found that when using a hyaluronate of very high molecular weight, as e.g. about 4,000,000, the best results are obtained at concentration from about 0.05 to 2 mg/ml and that when using a hyaluronate of lower molecular weight, as e.g. about 200,000 the best results are obtained at concentrations from about 0.05 to 4 mg/ml and that the preferred ranges in these cases are 0.1 to 2, e.g. 0.5 to 1.5 mg/ml. The experimental work has indicated that the molecular weight is not a critical parameter when preparing penetration media according to the invention at least not e.g. within the range of about 100,000 to 7,000,000.

What has been said at the outset regarding the method of separating motile sperm cells and regarding the aqueous artificial penetration medium employed for this purpose applies also to the method and medium according to the present invention. Thus for instance the improved medium of the invention, too, is given pH values within a range that is suitable for sperm and physiologically acceptable to them (e.g. by means of adding a physiologically acceptable buffer, e.g. a phosphate or bicarbonate buffer, as for instance a sodium phosphate buffer, to give a physiologically normal pH value); this improved medium may contain physiologically acceptable substances (e.g. one or more substances selected from one or more of the following groups: salts such as chlorides, acetates, lactates etc. of sodium, potassium and calcium, the positive ion concentrations chosen being preferably physiological concentrations; nutrients such as glucose, galactose; protein such as albumin; serum, preferably heat-inactivated at 56° C. for 30 min.; optionally equilibration with air containing $CO_2$, e.g. 5 %; etc.) as has been explained in the introduction to this specification; also the osmotic pressure of the medium may be regulated so as to acquire a value suitable for the sperm.

The medium according to the invention may be produced by incorporating a water-soluble physiologically acceptable salt of hyaluronic acid into the above-described aqueous artificial penetration medium for sperm. (The hyaluronate average molecular weight and its concentration, as well as the viscosity of the medium, may be chosen as described above.) The order in which the components are added when the aqueous solution is being prepared may of course be varied without departure from the inventive concept. The penetration medium with its desired concentration of hyaluronate may be prepared aseptically or may be sterilized if desired. The medium may be presented in the form of disposable unit packages, or in the form of larger packs containing a larger volume of the medium sufficient for a plurality of sperm selection operations.

The improved medium according to the present invention makes the process of this invention very dependable, giving reliable and reproducible sperm screening results. The medium is favourable to sperm; long survival periods may be obtained with sperm cells that have migrated in the medium, as e.g. survival periods exceeding 2 hours, for instance exceeding 4 hours, When sperm upon having migrated in the medium are used for fertilization a high fertilizing degree will be obtained. The medium furthermore is substantially unharmful vis-é-vis the egg.

The invention will be elucidated further by means of the below examples which however do not limit the scope of the invention.

EXAMPLE 1

(a) 0.75 volume of human serum, heat-inactivated for 30 min. at 56° C., is added to 10 volumes of Ham's F10 medium (available commercially e.g. from Sigma Chemical Company, St Louis, Mo., USA and described in e.g. an article by R. G. Ham in Exptl. Cell. Res. 39(1963) p. 515) supplemented with 0.5 mg/ml sodium hyaluronate ($\overline{M}_w$ about 4,000,000) and pH adjusted to 7.4. This penetration medium is kept under air containing 5 % $CO_2$ for e.g. half an hour at 37° C. before use.

(b) The same medium as in Example 1 (a) but with 0.3 mg/ml sodium hyaluronate. ($\overline{M}_w$ about 4,000,000.)

(c) The same medium as in Example 1 (a) but with 0.8 mg/ml sodium hyaluronate. ($\overline{M}_w$ about 4,000,000.)

(d) The same medium as in Example 1 (a) but without any addition of serum; instead, 5 mg/ml human serum albumin is used.

(e) 1 ml of a solution containing 2 mg sodium hyaluronate ($\overline{M}_w$ about 3,600,000) and 8.5 mg NaCl and being 0.002M in sodium phosphate (pH 7.4) is mixed with 1 ml Earle's balanced salt solution (e.g. from Sigma Chemical Company as above) and 0.1 ml human serum (heat-inactivated for 30 min at 56° C.). The penetration medium thus obtained is kept under air containing 5% $CO_2$ at 37° C. for 30 min and the pH value is adjusted to about 7.4.

A series of penetration media were prepared analogously to the examples given above, covering concentrations in the range of from 0.05 to 8 mg/ml, of hyaluronate with molecular weight of from 130,000 to 7,000,000. In some experiments Earle's medium (obtainable from e.g. Sigma Chemical Company as above) or some other cell culture medium was used.

The result of the penetration tests carried out indicated that when using hyaluronate of high molecular weight, for instance higher than about 1,000,000, the best results are obtained at concentrations from about 0.05 to 2 mg/ml. When using low molecular weight hyaluronate ($\overline{M}_w$ for example 160,000) the concentration can be increased to about 4 mg/ml. A preferred range is 0.1–2 mg/ml, especially 0.5 to 1.5 mg/ml, for diagnostic tests.

EXAMPLE 2

To carry out sperm penetration experiments one may employ for example a capillary tube (e.g. 4–7 cm length and having an interior volume of 10 μl). The capillary tube is filled with the improved penetration medium of this invention (e.g. a medium prepared analogously to Example 1). The upper opening of the capillary tube is sealed, and the lower portion of the tube is introduced into a small vessel containing a sample of ejaculate. Sperm penetration into the capillary tube is allowed to proceed for e.g. 1 hour at 37° C. (If desired this may take place under air containing 5% $CO_2$.) Sperm penetration can be observed in a microscope; the distance which the sperm have covered by their migration is measured, and from the measured value their rate of migration is calculated (suitably in μm/sec). In this manner it is possible for instance to calculate the rate of migration of those sperm that have outdistanced the others, to thus obtain so-called top values, and also to calculate the migration rate of the bulk of all the other sperm cells that have entered into the medium, this value being the so-called base value. Moreover it is possible to estimate the amount of sperm cells that have migrated at a rate close to the top value. For example, the top value may be 9.6 μm/sec and the base value e.g. 4–6 μ/sec. Parallel tests will give values of good reproducibility. The penetration test may be utilized for e.g. diagnostic purposes.

EXAMPLE 3

Short Pasteur pipettes are sealed at their tip by fusion. 0.25 ml of ejaculate sample is inserted at the bottom of the sealed pipette tube while the tube is being maintained in a vertical position. 0.25 ml of the improved penetration medium according to the invention (e.g. according to Example 1) is layered carefully onto the sperm-containing bottom phase. Penetration of sperm cells from the bottom phase into the overlayer of penetration medium is allowed to proceed at 37° C. (If desired this may take place under air containing 5% $CO_2$.) When sperm cells have migrated upwardly into the upper portion of the penetration layer, as e.g. after 60 minutes, the upper portion, corresponding to e.g. ⅔ of the whole penetration layer, is cautiously removed by aspiration. The sample thus withdrawn contains motile sperm cells. The sperm present in this sample may be put to use for fertilization purposes (e.g. for in vitro fertilization) in a manner known per se.

We claim:

1. In a process for separating motile sperm cells in vitro from an aqueous sperm-containing sample that involves contacting said sample with a layer of an aqueous artificial penetration medium for sperm cells, whereby motile sperm cells are caused to migrate from said sperm-containing sample into said layer, the improvement comprising that a water-soluble physiologically acceptable salt of hyaluronic acid has been incorporated in said penetration medium.

2. A process according to claim 1 wherein the sperm cells which have migrated into said layer of artificial penetration medium are separated and recovered for fertilization.

3. A method for fertilization which comprises using in the fertilization procedure a sperm sample from an artificial penetration medium containing a water-soluble physiologically acceptable salt of hyaluronic acid, into said motile sperm cells have been caused to migrate.

* * * * *